United States Patent [19]

Cohen et al.

[11] Patent Number: 5,108,957

[45] Date of Patent: Apr. 28, 1992

[54] GLASS FIBERS DECOMPOSABLE IN A PHYSIOLOGICAL MEDIUM

[75] Inventors: Isabelle Cohen, Chambery; Sylvie Thelohan, Paris, both of France; Hans Furtak, Speyer am Rhein; Hartmut Tiesler, Bockenheim, both of Fed. Rep. of Germany

[73] Assignee: Isover Saint-Gobain, Courbevoie, France

[21] Appl. No.: 565,282

[22] Filed: Aug. 9, 1990

[30] Foreign Application Priority Data

Aug. 11, 1989 [FR] France ............................ 89 10834
Feb. 9, 1990 [FR] France ............................ 90 01497

[51] Int. Cl.$^5$ ............... C03C 13/00; C03C 3/097; C03C 3/089; C03C 3/091
[52] U.S. Cl. ............... 501/35; 501/58; 501/59; 501/63; 501/65; 501/66
[58] Field of Search ............ 501/35, 58, 59, 63, 501/65, 66

[56] References Cited

U.S. PATENT DOCUMENTS

| | | | |
|---|---|---|---|
| 3,013,888 | 12/1961 | de Lajarte | 501/35 |
| 3,328,142 | 6/1967 | Lévecque | 501/35 |
| 3,513,002 | 5/1970 | Labino | 501/35 |
| 3,853,569 | 10/1974 | Laurent et al. | 501/35 |
| 4,312,952 | 1/1982 | Carbol | 501/36 |
| 4,381,347 | 4/1983 | Carbol | 501/36 |
| 4,615,988 | 10/1986 | LeMoigne et al. | 501/30 |
| 4,756,732 | 8/1988 | Barthe et al. | 65/6 |
| 4,759,785 | 8/1988 | Barthe et al. | 65/6 |
| 4,759,974 | 8/1988 | Barthe et al. | 428/224 |

FOREIGN PATENT DOCUMENTS

2080281 2/1982 United Kingdom ............ 501/35

OTHER PUBLICATIONS

Chemical Abstract, vol. 98, No. 8 (Feb. 21, 1983) #58810d.
Chemical Abstract, vol. 81, No. 26 (Dec. 1974) #175133v.
Chemical Abstract, vol. 84, No. 12 (Mar. 22, 1976) #78592y-78607g.
Chemical Abstract, vol. 108, No. 8 (Feb. 1988) #61226y.

*Primary Examiner*—Mark L. Bell
*Attorney, Agent, or Firm*—Pennie & Edmonds

[57] ABSTRACT

Glass compositions useful for forming fibers which are readily able to be degraded in a physiological medium such as that found in a human body. Advantageous compositions formed according to the present invention comprise the following components, set forth in percent by weight:

$SiO_2$: 57 to 70%
$Al_2O_3$: 0 to 5%
$CaO$: 5 to 10%
$MgO$: 0 to 5%
$Na_2O + K_2O$: 13 to 18%
$B_2O_3$: 2 to 12%
$F$: 0 to 1.5%
$P_2O_5$: 0 to 4%
Impurities: less than 2%

5 Claims, No Drawings

GLASS FIBERS DECOMPOSABLE IN A PHYSIOLOGICAL MEDIUM

FIELD OF THE INVENTION

The present invention relates to compositions of glass, and more particularly, to the formation of glass fibers which, by virtue of their composition, are decomposable upon contact with a physiological medium, such as that found within a human body.

BACKGROUND OF THE INVENTION

Mineral fibers, such as glass fibers are often incorporated into thermal and acoustic insulating materials used in the construction industry. The particular configuration of the premises to be insulated often necessitates that these insulation materials be cut and/or shaped at the job site. This operation, however, typically causes breakage of the glass fibers and the possible dispersion of these broken fragments into the surrounding atmosphere. It follows, therefore, that at times there is a danger of accidental inhalation of these fiber fragments by those who come into contact with them. Although these fibers and/or broken fragments have not been demonstrated to be harmful, the need is felt to reassure those working with these materials by offering a demonstrably safe product.

SUMMARY OF THE INVENTION

An object of the present invention is the formation of glass fibers which are quickly and readily degraded when placed in contact with a physiological medium. By a "physiological medium", applicants mean a medium such as that typically found within a human body.

A further object of the invention is to provide glass compositions which may be formed into such decomposable fibers by the use of traditional fiber-forming techniques, such as centrifugation.

The conditions under which such fibers are used are most restrictive when the fibers are formed by so-called "inner" centrifuging techniques. By inner centrifuging techniques, we mean those techniques in which the molten material exits the centrifuge through small, peripherally located orifices. Such compositions are worked at relatively low temperatures so as to extend the life expectancy of both the material itself and the centrifuge used to form the fibers.

Moreover, during the centrifuging operation, the liquidus temperature, i.e., that temperature at which the growth rate of crystals within the glass becomes zero, which is characteristic of the devitrification of the glass, must be kept lower than the temperature at which the glass fiber is drawn from the centrifuge. This minimizes the risk of crystal formation within the centrifuge. Such crystals might otherwise block the orifices of this apparatus and thus prevent the glass from exiting.

The objects of the present invention are achieved by modifying glass compositions comprising silica, alumina, alkaline and alkaline-earth oxides and boric anhydride. It has been determined that, by reducing or even eliminating the amount of alumina in the composition of the glass and optionally adding a sufficient amount of phosphorous pentoxide, it is possible to obtain glasses which, for example, when formed into fibers, are quickly degraded in a physiological medium such as that found in a human body.

It has further been found that glass products formed according to the present invention do not suffer any substantial diminution of their properties in comparison to those of prior art glass products, i.e., those which are only slightly or not at all decomposable in a physiological medium. Thus, the presently disclosed glass compositions can readily be transformed into fibrous products using standard centrifuging techniques. Moreover, even though the glass compositions of the invention optionally comprise a phosphorous-containing component, they may be formed in standard glass-forming furnaces without causing excessive wear of the refractory surface within these furnaces The glass fibers formed according to the present invention comprise the following components (in weight percent):

$SiO_2$: 57–70%
CaO: 5–10%
$Na_2O + K_2O$: 13–16%
$B_2O_3$: 2–12 %
Impurities: <2%

Optionally, the compositions described above may also comprise one or more of the following additional components in the amounts noted below (in weight %):

$Al_2O_3$: 0–5%
MgO: 0–5%
F: 0–1.5%
$P_2O_5$: 0–4% wherein the amount of $P_2O_5$ is greater than 0.1% by weight when the amount of $Al_2O_3$ is greater than or equal to about 1% by weight.

The compositions defined above may be prepared from substantially pure components but generally they are obtained by melting a mixture of natural raw materials containing various impurities.

DESCRIPTION OF THE PREFERRED EMBODIMENTS

The preferred ranges of components for glass fibers formed according to the present invention, designated as A and B, are set forth below. The amount of each component is given in percent by weight.

| Component | A | B |
| --- | --- | --- |
| $SiO_2$ | 59–68% | 60–68% |
| $Al_2O_3$ | 0–3% | 1–5% |
| CaO | 6–9% | 6–9% |
| MgO | 2–4% | 2–4% |
| $Na_2O$ | 14–17% | 14–17% |
| $K_2O$ | 0–2% | 0–2% |
| $B_2O_3$ | 4–11% | 4–11% |
| F | 0–1.5% | 0–1.5% |
| $P_2O_5$ | 0–3% | 0.5–4% |

To permit the use of outer centrifuging techniques with these materials, the compositions described above advantageously exhibit a suitable viscosity at a relatively low temperature. Preferably, these compositions should reach a viscosity of 1,000 cps at a temperature lower than about 1200° C and preferably lower than about 1150° C.

Another physical characteristic that is relevant to the production of glass fibers formed from the compositions set forth herein is the temperatures associated with the devitrification phenomenon, i.e., the formation of crystals within the glass. This phenomenon may be characterized on the basis of several temperatures, i.e., the temperature at which the growth rate of the crystals is at its maximum; and the liquidus temperature, i.e., as noted above the temperature at which the growth rate of the crystals is reduced to zero.

Moreover, it is desirable that the difference between the temperature at which a viscosity of 1,000 cps is achieved in the glass and the liquidus temperature be greater than about 50° C.

The advantages of the present invention are clearly illustrated in the following series of tests, the results of which are provided solely to promote a better understanding of the invention and which should not be viewed as limiting the invention in any manner.

EXAMPLES

Test Series No. 1

(comparative)

Table 1 sets forth several compositions used in the prior art for the production of glass fibers. Composition 1 is a traditional composition used in the production of insulation fibers, particularly those formed by centrifuging techniques. Composition 2 is of a type typically used with outer centrifuging techniques. Composition 3 has been used in the production of glass fibers drawn by gas streams.

To test the degradability of glass fibers in a physiological medium, the glass fibers were mechanically drawn to a diameter of 10 micrometers according to the "textile process", which is well known in the art, using a laboratory die having a single orifice.

The obtained fibers were then immersed in a solution simulating a buffered physiological medium having the following chemical composition (expressed in grams per liter):

NaCl: 6.78
$NH_4Cl$: 0.535
$NaHCO_3$: 2.268
$NaH_2PO_4H_2O$: 0.166
($Na_3$ citrate) $2H_2O$: 0.059
Glycine: 0.450
$H_2SO_4$: 0.049
$CaCl_2$: 0.022

The degradability of these glass fibers was tested in the physiological solution under the following conditions: 30 milligrams of fibers were immersed in 30 milliliters of solution maintained in a closed environment (i.e., under batch conditions) at a temperature of 37° C. for 3, 10 and 32 days. At the end of each of these periods, the concentration of the silica dissolved in the solution was measured. This concentration is expressed in milligrams per liter.

The hydrolytic resistance of these materials was also measured to provide additional data for purposes of comparison. These measurements were performed according to a standard method known as the "DGG Method". The DGG Method, as is known in the art, comprises immersing 10 grams of ground glass, having a grain size of between about 360-400 micrometers, in 100 milliliters of water at the boiling point for 5 hours. After quickly cooling the material, the solution is filtered and a given volume of the filtrate is evaporated to dryness. The weight of the dry material thus obtained makes it possible to calculate the amount of glass dissolved in the water. This amount is expressed in milligrams per gram of glass tested.

The results of the measurements of degradability and DGG are set forth in Table 2 for each of the compositions described in Table 1. Based upon these results, it was determined that the degradation of the fibers in the physiological solution is very variable from one glass composition to another. Of the three compositions tested, only no. 1 exhibits any noticeable degradation, but even this degradation is slight compared to that obtained with fibers formed of glass composition disclosed according to the present invention. Glass compositions no. 2 and 3 were only very slightly attacked.

Test Series No. 2

This series of tests was performed using various compositions of glass fibers formed according to the present invention. These compositions, formed as set forth in Table 3, correspond to glass composition nos. 4-11. Glass no. 1, the composition of which is described in Table 1, was utilized for purposes of comparison. Using these compositions, i.e., nos. 1 and 4-11, fibers having a diameter of 10 micrometers were drawn under the conditions outlined in the first series of tests.

The chemical resistance of these fibers to the effects of a physiological medium and their hydrolytic resistance (i.e., DGG value) were measured under conditions identical to those described in the first series of tests. The degree of degradation of the fibers was measured by determining the concentration of silica dissolved in the physiological solutions over various periods, i.e., 3, 6 and 10 days.

It is important to emphasize that, since the fiber degradation measurement was performed in a discrete batch of the physiological medium, rather than a continuous flow, the rate of degradation of the fibers should be measured beyond the period set for the end of the test because, under batch conditions the rate of attack slows down. This is because fresh solution is not constantly provided, such as occurs in real life conditions within the human body. It has thus been determined that the concentrations of dissolved silica measured at the end of the shortest attack periods best reflects the capability for the fibers to be degraded in a physiological medium. The results obtained are set forth in Table 4.

Glass composition nos. 4, 5, 7 and 8 illustrate the influence of $P_2O_5$ on the rate at which the fibers whose compositions contain the same percentage of $B_2O_3$ are attacked by the physiological solution. After 3 days, composition nos. 4 and 5, which contain a rather high percentage of phosphorous, were found to decompose four to five times faster than glass composition no. 1, which was used as a reference. Glass composition nos. 4, 7 and 8 illustrate that in glasses with a constant alumina content, the rate of decomposition diminishes with the phosphorous content.

Glass composition nos. 5 and 10 have the same percentage of $Al_2O_3$ but contain different percentages of $P_2O_5$. Although the decomposition rate of glass composition no. 10 is slightly lower than that of glass composition no. 5, this difference is not as large as the differences between the percentages of $P_2O_5$ in the two compositions could justify. It thus appears that the $B_2O$ content of the glass, which is higher in composition no. 10, compensates, at least in part, for the reduction in the percentage of $P_2O_5$.

The influence of $B_2O_3$ is confirmed by glass composition nos. 9 and 11 which contain a high percentage of this oxide. Composition no. 9 exhibits a good rate of decomposition despite having a fairly high percentage of $Al_2O_3$. Glass composition no. 11 has a high decomposition rate when compared to composition no 10, which is due both to the reduction in the $Al_2O_3$ content and to the high percentage of $B_2O_3$.

The presence of phosphorous in glass compositions formed according to the present invention has the effect of increasing the rate of decomposition of the fibers in a physiological medium. It has also been found, however, that simply reducing or even eliminating the alumina oxide from the glass can also cause the composition to have a high decomposition rate in a physiological medium. This is demonstrated by glass composition no. 6 which has essentially no alumina, except that which is present in the form of impurities provided by raw materials supplying other components of the glass.

Although the presence of phosphorous in glasses formed according to the invention is generally desirable, it is not essential when the alumina content does not exceed about 1% by weight. It is therefore preferable that the composition of the glass fibers contain more than 0.1% by weight of phosphorous pentoxide. Moreover, in glass composition having 2% or more of $Al_2O_3$ the percentage of $P_2O_5$ should be at least about 0.5% by weight.

To prevent accelerated wear on the refractory linings of the melting furnaces used to form the glass compositions of the present invention, it is desirable that the percentage of $P_2O_5$ not be greater than about 4%. In the preferred compositions of the invention, the percentage of this oxide should be less than or equal to about 3%, such that the percentage of alumina does not exceed about 3%.

Thus, the glass compositions formed according to the present invention have viscosities and devitrification characteristics comparable to those of known glass compositions e.g., composition no. 1 (see Tables 5 and 6).

The glass compositions of the present invention therefore offer the advantage of being able to be formed into fibers in traditional installations, such as those using the "inner" centrifuging technique. This technique is described in a number of references, such as U.S. Pat. Nos. 3,020,586; 3,304,164; 2,949,632 and 3,523,774, the disclosure of each of which is incorporated herein by reference. As discussed above and as disclosed in these references, this technique comprises feeding molten glass to a centrifuge provided with a peripheral wall having a plurality of orifices. Due to the effects of centrifugal force, the molten glass passes through the orifices and is thereafter transformed into fibers under the effects of jets of hot gas.

The fibers thus obtained may be used to form high-quality fibrous products suitable for numerous applications. For example, these fibers may advantageously be used in the form of felts or geometrically well-defined panels, stiffened by a polymerized bonding material, or in the form of tubular products intended, e.g., for duct insulation. Glass fibers formed according to the invention can also be used in the form of mats sewn on cardboard or metal netting in the form of pads, or even in bulk form, i.e., by filling.

While it is apparent that the invention herein disclosed is well calculated to fulfill the objectives stated above, it will be appreciated that numerous modifications and embodiments may be devised by those skilled in the art. It is intended that the appended claims cover all such modifications and embodiments as fall within the true spirit and scope of the present invention.

TABLE NO. 1

| Known Compositions (in percentages in weight) | | | |
|---|---|---|---|
| Components | Glass no. 1 | Glass no. 2 | Glass no. 3 |
| $SiO_2$ | 65.01 | 44.50 | 59.00 |
| $Fe_2O_3$ | 0.45 | 3.90 | 0.17 |
| $Al_2O_3$ | 3.40 | 13.80 | 5.50 |
| CaO | 7.00 | 27.80 | 2.00 |
| MgO | 2.95 | 7.00 | 0.30 |
| $Na_2O$ | 15.85 | 1.30 | 11.20 |
| $K_2O$ | 0.70 | 0.60 | 1.60 |
| $B_2O_3$ | 4.50 | | 11.00 |
| F | | | 1.00 |
| BaO | | | 5.00 |
| ZnO | | | 3.50 |

TABLE No. 2

| Chemical Resistance in a Physiological Medium and in Water | | | |
|---|---|---|---|
| $SiO_2$ in mg/l | Glass no. 1 | Glass no. 2 | Glass no. 3 |
| 3 days | 19.5 | 1.3 | 3.2 |
| 10 days | 55.6 | 2.6 | 31.7 |
| 32 days | 117.6 | 2.8 | 47.1 |
| DGG mg/g | 18.00 | 9.0 | 7.5 |

TABLE No. 3

| Compo-nents | Glass Compositions (in percentages by weight) | | | | | | | | |
|---|---|---|---|---|---|---|---|---|---|
| | Glass no. 1 | Glass no. 4 | Glass no. 5 | Glass no. 6 | Glass no. 7 | Glass no. 8 | Glass no. 9 | Glass no. 10 | Glass no. 11 |
| $SiO_2$ | 65.01 | 65.51 | 65.33 | 69.90 | 64.95 | 63.80 | 59.50 | 64.28 | 60.90 |
| $Al_2O_3$ | 3.40 | 3.40 | 2.05 | 0.13 | 3.30 | 3.30 | 4.90 | 2.10 | 1.10 |
| CaO | 7.00 | 7.00 | 7.00 | 7.00 | 6.90 | 6.90 | 7.00 | 7.00 | 6.90 |
| MgO | 2.95 | 2.95 | 3.00 | 2.90 | 2.90 | 2.90 | 2.95 | 2.95 | 2.85 |
| $Na_2O$ | 15.85 | 15.85 | 15.50 | 15.60 | 15.50 | 15.60 | 13.85 | 15.85 | 15.90 |
| $K_2O$ | 0.70 | 0.70 | 0.08 | 0.07 | 0.60 | 0.60 | 0.70 | 0.60 | 0.60 |
| $B_2O_3$ | 4.50 | 4.50 | 4.25 | 4.10 | 4.70 | 4.60 | 9.75 | 5.90 | 10.20 |
| $P_2O_5$ | — | 3.40 | 2.45 | — | 1.00 | 2.00 | 1.00 | 1.00 | 1.15 |
| others | 0.59 | 0.69 | 0.34 | 0.30 | 0.30 | 0.15 | 0.30 | 0.32 | 0.40 |

TABLE No. 4

| | Chemical Resistance in a Physiological Medium Concentration of Dissolved $SiO_2$ (in mg/l) | | | | | | | | |
|---|---|---|---|---|---|---|---|---|---|
| Attack time | Glass no. 1 | Glass no. 4 | Glass no. 5 | Glass no. 6 | Glass no. 7 | Glass no. 8 | Glass no. 9 | Glass no. 10 | Glass no. 11 |
| 3 days | 19.5 | 96.3 | 83.4 | 128.3 | 72.7 | 74.9 | 80.2 | 75.1 | 105.0 |
| 6 days | | | | 149.7 | 106.9 | 104.8 | 103.5 | 105.4 | 128.1 |
| 10 days | 55.6 | 132.7 | 132.7 | 172.6 | 124.1 | 128.3 | 119.4 | 127.6 | 147.6 |
| 32 days | 117.6 | 143.0 | 139.0 | — | — | — | — | — | — |

TABLE No. 5

| Viscosity | Viscosity Temperatures - Characteristics (in °C.) | | | | | | | | |
|---|---|---|---|---|---|---|---|---|---|
| | Glass no. 1 | Glass no. 4 | Glass no. 5 | Glass no. 6 | Glass no. 7 | Glass no. 8 | Glass no. 9 | Glass no. 10 | Glass no. 11 |
| $\log n = 3$ | 1075 | — | 1099 | 1095 | 1092 | 1089 | 1030 | 1061 | 1003 |
| $\log n = 2.5$ | 1173 | — | 1201 | 1197 | 1195 | 1191 | 1133 | 1164 | 1090 |

TABLE No. 6

| T# (#C) | Devitrification Characteristics | | | | | | | | |
|---|---|---|---|---|---|---|---|---|---|
| | Glass no. 1 | Glass no. 4 | Glass no. 5 | Glass no. 6 | Glass no. 7 | Glass no. 8 | Glass no. 9 | Glass no. 10 | Glass no. 11 |
| Liquidus | 910 | — | 870 | 930 | 970 | 825 | — | 870 | 850 |
| Max. rate | 830 | — | 780 | 820 | 810 | 800 | — | 800 | 795 |
| Max rate (/mn) | 0.65 | — | 0.05 | 0.51 | 0.19 | 0.11 | — | 0.10 | 0.11 |

TABLE No. 7

| Hydrolytic Resistance - DGG (in mg/g) | | | | | | | | |
|---|---|---|---|---|---|---|---|---|
| Glass no. 1 | Glass no. 4 | Glass no. 5 | Glass no. 6 | Glass no. 7 | Glass no. 8 | Glass no. 9 | Glass no. 10 | Glass no. 11 |
| 18.0 | 16.0 | 25.0 | 51.0 | 19.2 | 18.7 | 16.1 | 20.5 | 32 |

We claim:

1. Glass fiber which is decomposable in a physiological medium, said fiber comprising:
  $SiO_2$: 57 to 70 wt %;
  CaO: 5 to 10 wt %;
  $Na_2O + K_2O$: 13 to 18 wt %;
  $B_2O_3$: 2 to 12 wt %;
  $Al_2O_3$: up to about 5 wt %;
  MgO: up to about 5 wt %;
  F: up to about 1.5 wt %;
  Impurities: less than 2 wt %; and
  $P_2O_5$ in an amount effective in combination with the $B_2O_3$ and, when present, the $Al_2O_3$, but less than about 4 wt. %, to cause the fiber to be decomposable in a physiological midi; wherein said fiber contains more than 0.1% by weight of $P_2O_5$ when the percentage by weight of alumina is greater than or equal to about 1%.

2. The fiber of claim 1 which comprises at least about 0.5% by weight of $P_2O_5$ when the amount of alumina in said fiber is at least about 2% by weight.

3. Glass fiber which is decomposable in a physiological medium, said fiber comprising:
  $SiO_2$: 59 to 68 wt %;
  CaO: 6 to 9 wt %;
  MgO: 2 to 4 wt %;
  $Na_2O$: 14 to 17 wt %;
  $Al_2O_3$: up to about 3 wt %;
  $K_2O$: up to about 2 wt %;
  F: up to about 1.5 wt %;
  $B_2O_3$: 4 to 11 wt %; and
  $P_2O_5$ in an amount effective in combination with the $B_2O_3$ and, when present, the $Al_2O_3$ but less than about 4 wt., % to cause the fiber to be decomposable in a physiological medium, wherein said fiber contains more than 0.1% by weight of $P_2O_5$ when the percentage by weight of alumina is greater than or equal to about 1%.

4. Glass fiber decomposable in a physiological medium, said fiber comprising:
  $SiO_2$: 60 to 68 wt %;
  $Al_2O_3$: 1 to 5 wt %;
  CaO: 6 to 9 wt %;
  MgO: 2 to 4 wt %;
  $Na_2O$: 14 to 17 wt %;
  $B_2O_3$: 4 to 11 wt %;
  $P_2O_5$: 0.5 to 4 wt %;
  $K_2O$: up to about 2 wt %; and
  F: up to about 1.5 wt %;
  wherein the amounts of $P_2O_5$, $B_2O_3$ and $Al_2O_3$ are effective to cause the fiber to be decomposable in a physiological medium.

5. An insulating material comprising the glass fiber of any one of claims 1, 2 or 4.

* * * * *